United States Patent
Lozier et al.

(10) Patent No.: US 8,029,566 B2
(45) Date of Patent: Oct. 4, 2011

(54) IMPLANT SENSORS

(75) Inventors: Antony J. Lozier, Warsaw, IN (US);
David B. Rich, Warsaw, IN (US);
Russell M. Parrott, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 553 days.

(21) Appl. No.: 12/131,188

(22) Filed: Jun. 2, 2008

(65) Prior Publication Data
US 2009/0299228 A1    Dec. 3, 2009

(51) Int. Cl.
*A61F 2/28*    (2006.01)
(52) U.S. Cl. .................. 623/16.11; 600/424; 442/209
(58) Field of Classification Search .................. None
See application file for complete search history.

(56) References Cited

U.S. PATENT DOCUMENTS

| | | | |
|---|---|---|---|
| 3,374,787 A * | 3/1968 | Hatke | 128/839 |
| 3,915,015 A | 10/1975 | Crane et al. | |
| 4,503,705 A | 3/1985 | Polchanioff | |
| 4,822,362 A | 4/1989 | Walker et al. | |
| 4,997,445 A | 3/1991 | Hodorek | |
| 5,085,252 A | 2/1992 | Mohamed et al. | |
| 5,197,488 A | 3/1993 | Kovacevic | |
| 5,326,363 A | 7/1994 | Aikins | |
| 5,360,016 A | 11/1994 | Kovacevic | |
| 5,399,418 A * | 3/1995 | Hartmanns et al. | 428/218 |
| 5,412,619 A | 5/1995 | Bauer | |
| 5,425,775 A | 6/1995 | Kovacevic et al. | |
| 5,456,724 A | 10/1995 | Yen et al. | |
| 5,465,760 A | 11/1995 | Mohamed et al. | |
| 5,470,354 A | 11/1995 | Hershberger et al. | |
| 5,518,008 A | 5/1996 | Cucchiaro et al. | |
| 5,529,070 A | 6/1996 | Augustine et al. | |
| 5,645,077 A | 7/1997 | Foxlin | |
| 5,678,448 A | 10/1997 | Fullen et al. | |
| 5,719,324 A | 2/1998 | Thundat et al. | |
| 5,733,292 A | 3/1998 | Gustilo et al. | |
| 5,777,467 A | 7/1998 | Arms et al. | |
| 5,807,284 A | 9/1998 | Foxlin | |
| 5,840,047 A | 11/1998 | Stedham | |
| 5,876,325 A | 3/1999 | Mizuno et al. | |
| 5,879,398 A | 3/1999 | Swarts et al. | |

(Continued)

FOREIGN PATENT DOCUMENTS

DE    4017646 A1    12/1991

(Continued)

OTHER PUBLICATIONS

Cooper et al., James A. Fiber-Based Tissue-Engineered Scaffold For Ligament Replacement: Design Considerations and in Vitro Evaluation, *Biomaterials* 26 (2005) 1523-1532, Elsevier Ltd. @ www.elsevier.com/locate/biomaterials.

(Continued)

*Primary Examiner* — Corrine M McDermott
*Assistant Examiner* — Megan Wolf
(74) *Attorney, Agent, or Firm* — Baker & Daniels LLP

(57) ABSTRACT

Exemplary orthopedic implants are disclosed. The orthopedic implants may include one or more sensors. Exemplary sensors include sensors to monitor bone growth, changes to the implant over time, and proper placement of the implant. The orthopedic implants may include a woven material. Sensor arrangements to detect a state of an item are disclosed. Exemplary states include folded, unfolded, and inflated. Exemplary items include an orthopedic implant and a parachute.

11 Claims, 14 Drawing Sheets

U.S. PATENT DOCUMENTS

| | | | |
|---|---|---|---|
| 5,941,904 A | 8/1999 | Johnston et al. | |
| 6,034,296 A | 3/2000 | Elvin et al. | |
| 6,122,538 A | 9/2000 | Sliwa, Jr. et al. | |
| 6,122,541 A | 9/2000 | Cosman et al. | |
| 6,129,122 A | 10/2000 | Bilisik | |
| 6,143,035 A | 11/2000 | McDowell | |
| 6,162,191 A | 12/2000 | Foxlin | |
| 6,165,135 A | 12/2000 | Neff | |
| 6,216,537 B1 | 4/2001 | Henschel et al. | |
| 6,245,109 B1 | 6/2001 | Mendes et al. | |
| 6,281,149 B1 | 8/2001 | Hussein et al. | |
| 6,283,168 B1 | 9/2001 | Gu et al. | |
| 6,285,902 B1 | 9/2001 | Kienzle et al. | |
| 6,307,481 B1 | 10/2001 | Lehrman et al. | |
| 6,315,007 B1 | 11/2001 | Mohamed et al. | |
| 6,345,598 B1 | 2/2002 | Bogdanovich et al. | |
| 6,361,507 B1 | 3/2002 | Foxlin | |
| 6,425,923 B1 | 7/2002 | Stalcup et al. | |
| 6,439,096 B1 | 8/2002 | Mungalov et al. | |
| 6,447,448 B1 | 9/2002 | Ishikawa et al. | |
| 6,447,886 B1 | 9/2002 | Mohamed et al. | |
| 6,474,159 B1 | 11/2002 | Foxlin et al. | |
| 6,513,381 B2 | 2/2003 | Fyfe et al. | |
| 6,523,392 B2 | 2/2003 | Porter et al. | |
| 6,553,681 B2 | 4/2003 | Ekholm et al. | |
| 6,567,703 B1 | 5/2003 | Thompson et al. | |
| 6,573,706 B2 | 6/2003 | Mendes et al. | |
| 6,583,630 B2 | 6/2003 | Mendes et al. | |
| 6,610,096 B2 | 8/2003 | MacDonald | |
| 6,611,141 B1 | 8/2003 | Schulz et al. | |
| 6,661,347 B2 | 12/2003 | Lehrman et al. | |
| 6,706,005 B2 | 3/2004 | Roy et al. | |
| 6,733,533 B1 | 5/2004 | Lozier | |
| 6,786,877 B2 | 9/2004 | Foxlin | |
| 6,820,025 B2 | 11/2004 | Bachmann et al. | |
| 6,909,985 B2 | 6/2005 | Stana | |
| 6,950,025 B1 | 9/2005 | Nguyen | |
| 7,000,469 B2 | 2/2006 | Foxlin et al. | |
| 7,028,547 B2 | 4/2006 | Shiratori et al. | |
| 7,097,662 B2 | 8/2006 | Evans, III et al. | |
| 7,104,130 B2 | 9/2006 | Kenny et al. | |
| 7,180,409 B2 | 2/2007 | Brey | |
| 7,195,645 B2 | 3/2007 | Disilvestro et al. | |
| 7,204,145 B2 | 4/2007 | Heinks et al. | |
| 7,325,453 B2 | 2/2008 | Bremer et al. | |
| 2001/0012932 A1 | 8/2001 | Peer | |
| 2002/0102743 A1 | 8/2002 | Majumdar et al. | |
| 2002/0104376 A1 | 8/2002 | Danyluk et al. | |
| 2002/0130673 A1 | 9/2002 | Pelrine et al. | |
| 2002/0180306 A1 | 12/2002 | Hunt et al. | |
| 2003/0003135 A1 | 1/2003 | Leung et al. | |
| 2003/0026758 A1 | 2/2003 | Baker | |
| 2003/0069591 A1 | 4/2003 | Carson et al. | |
| 2003/0069644 A1 | 4/2003 | Kovacevic et al. | |
| 2003/0119398 A1 | 6/2003 | Bogdanovich et al. | |
| 2004/0019384 A1 | 1/2004 | Kirking et al. | |
| 2004/0064191 A1 | 4/2004 | Wasielewski | |
| 2004/0080319 A1 | 4/2004 | Merrill | |
| 2004/0097952 A1 | 5/2004 | Sarin et al. | |
| 2004/0152970 A1 | 8/2004 | Hunter et al. | |
| 2004/0186576 A1 | 9/2004 | Biscup et al. | |
| 2004/0243148 A1 | 12/2004 | Wasielewski | |
| 2005/0010302 A1 | 1/2005 | Dietz et al. | |
| 2005/0068044 A1 | 3/2005 | Peine et al. | |
| 2005/0085915 A1* | 4/2005 | Steinberg | 623/17.16 |
| 2005/0116673 A1 | 6/2005 | Carl et al. | |
| 2005/0131390 A1 | 6/2005 | Heinrich et al. | |
| 2005/0146076 A1 | 7/2005 | Alexander et al. | |
| 2005/0165317 A1 | 7/2005 | Turner et al. | |
| 2005/0186081 A1 | 8/2005 | Mohamed | |
| 2005/0245817 A1* | 11/2005 | Clayton et al. | 600/424 |
| 2005/0245820 A1 | 11/2005 | Sarin | |
| 2005/0273170 A1 | 12/2005 | Navarro et al. | |
| 2006/0004431 A1 | 1/2006 | Fuller et al. | |
| 2006/0047283 A1 | 3/2006 | Evans et al. | |
| 2006/0058604 A1 | 3/2006 | Avinash et al. | |
| 2006/0075816 A1 | 4/2006 | Bremer et al. | |
| 2006/0142657 A1 | 6/2006 | Quaid et al. | |
| 2006/0150734 A1 | 7/2006 | Mimnagh-Kelleher et al. | |
| 2006/0235314 A1 | 10/2006 | Migliuolo et al. | |
| 2006/0254369 A1 | 11/2006 | Yoon et al. | |
| 2006/0271199 A1 | 11/2006 | Johnson | |
| 2007/0032748 A1 | 2/2007 | McNeil et al. | |
| 2007/0065077 A1 | 3/2007 | Childers et al. | |
| 2007/0189902 A1 | 8/2007 | Mohamed | |
| 2007/0219641 A1 | 9/2007 | Dorr et al. | |
| 2007/0225731 A1 | 9/2007 | Couture et al. | |
| 2007/0233258 A1 | 10/2007 | Hestad et al. | |
| 2007/0270686 A1 | 11/2007 | Ritter et al. | |
| 2007/0287911 A1 | 12/2007 | Haid et al. | |
| 2008/0010705 A1 | 1/2008 | Quaid et al. | |
| 2008/0010706 A1 | 1/2008 | Moses et al. | |
| 2008/0039868 A1 | 2/2008 | Tuemmier et al. | |
| 2008/0064947 A1 | 3/2008 | Heruth et al. | |
| 2008/0065225 A1 | 3/2008 | Wasielewski et al. | |
| 2008/0081982 A1 | 4/2008 | Simon et al. | |
| 2008/0097187 A1 | 4/2008 | Geilen et al. | |
| 2008/0123921 A1 | 5/2008 | Geilen et al. | |
| 2008/0130965 A1 | 6/2008 | Avinash et al. | |

FOREIGN PATENT DOCUMENTS

| | | |
|---|---|---|
| WO | WO03/002022 A2 | 1/2003 |
| WO | WO03/026518 A1 | 4/2003 |
| WO | WO03/071969 A1 * | 9/2003 |
| WO | WO03/077775 A1 * | 9/2003 |
| WO | WO2007/136784 A2 * | 11/2007 |

OTHER PUBLICATIONS

Shenfang, Yuan, Determination of Internal Strain in 3-D Braided Composites Using Optic Fiber Strain Sensors, *Acta Mechanica Solida Sinica*, vol. 17, No. 1, Mar. 2004, HUST, Wuhan, China.

Wang, Zhong Lin and Jinhui Song, Piezoelectric Nanogenerators Based on Zinc Oxide Nanowire Arrays, Science, vol. 312, Apr. 14, 2006 at www.sciencemag.org.

SCIENCE@NASA, The Right Stuff for Super Spaceships from http://science.nasa.gov/headlines/y2002/16sep_rightstuff.htmJul. 2, 2008.

T.K. Fehring et al., "Early Failures in Total Knee Orthoplasty," Clin Orthop. 2001, p. 315-318, vol. 382 (Fehring).*

F. Brick et al., "The Patellofemoral Component of Total Knee Arthroplasty," Clin Orthop. 1988, pp. 163-178, vol. 231 (Brick).*

G. Bergmann et al., "Hip Joint Loading During Walking and Running Measured in Two Patients," J of Biomechanics, 1993, pp. 969-990, vol. 26, Issue 8 (Bergmann1).*

G. Bergmann et al., "Frictional Heating of Total Hip Implants, Part 1 Measurement in Patents," J of Biomechanics, 2001, p. 421-428, vol. 34 (Bergmann2).*

G.M. Kotzar et al., "Telemeterized In Vivo Hip Joint Force Data: A report on Two Patients After Total Hip Surgery," J of Ortho Research, 1989, pp. 621-633, vol. 9, Issue 5 (Kotzar).*

D.T. Davy et al., "Telemetric Force Measurements Across the Hip after Total Arthroplasty," J of Bone and Joint Surgery, 1998, pp. 45-50, vol. 70-A, Issue 1 (Davy).*

K.R. Kaufman et al., "Instrumented Implant for Measuring Tibiofemoral Forces," J of Biomechanics, 1996, pp. 667-671, vol. 29, Issue 5 (Kaufman).

S.J.G. Taylor et al., "Forces and Moments Telemetered from two Distal Femoral Replacement During Various Activities," J of Biomech. 2001, pp. 829-848, vol. 34 (Taylor2).

P.F. Sharkey et al., "Why are Total Knee Anthroplasties Failing Today?," Clin Orthop, 2002, pp. 7-13, vol. 404 (Sharkey).

* cited by examiner

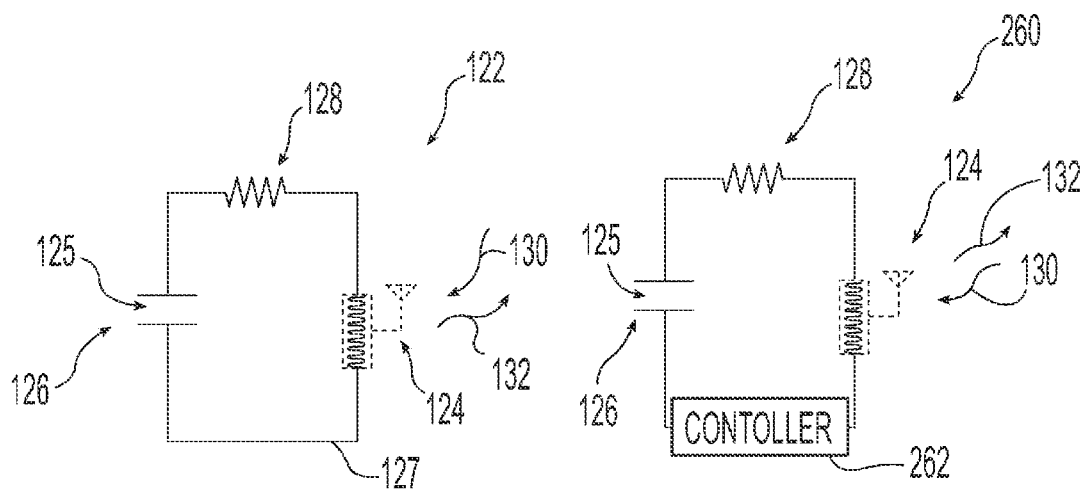
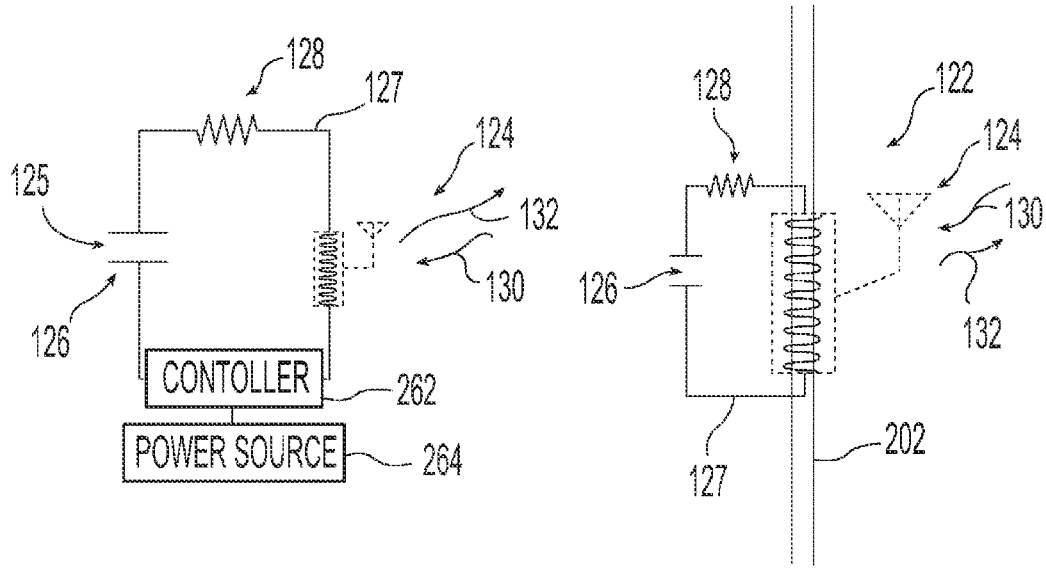
Fig. 14　　Fig. 15
Fig. 16　　Fig. 17

IMPLANT SENSORS

BACKGROUND AND SUMMARY OF THE INVENTION

The present invention relates generally to orthopedic implants and more particularly to orthopedic implants including one or more sensors.

Orthopedic implants are known. Further, it is known to implement inflatable orthopedic implants and to implement orthopedic implants including a woven portion.

The present invention relates to the use of one or more sensors with an orthopedic implant. The orthopedic implant may include one or more sensors for use during a surgical installation of the orthopedic implant. The orthopedic implant may include one or more sensors for use following a surgical installation of the orthopedic implant. The one or more sensors may include a passive sensor. The one or more sensors may include an active sensor.

In an exemplary embodiment of the present disclosure, an orthopedic implant for placement in a cavity formed in a bone is provided. The cavity having a predetermined shape. The orthopedic implant comprising a flexible body having an opening. The flexible body having an inflated state wherein said body has an outer shape generally corresponding to said predetermined shape formed in said bone and a non-inflated shape wherein said outer shape has a smaller envelope than said inflated state. The implant further comprising a plurality of sensors supported by said flexible body, said plurality of sensors providing an indication of whether said flexible body is in said inflated state or said non-inflated state; and a filler. The filler being positioned in said flexible body and causing said flexible body to transition from said non-inflated state to said inflated state.

In another exemplary embodiment of the present disclosure, an orthopedic implant for placement in a cavity having a predetermined shape formed in a bone is provided. The orthopedic implant comprising a flexible body having an inflated shape generally corresponding to said predetermined shape formed in said bone; means for sensing said shape of said flexible body; and a filler. The filler being positioned in said flexible body.

In a further exemplary embodiment of the present disclosure, a method of implanting an orthopedic implant in a cavity having a predetermined shape formed in a bone is provided. The method comprising the steps of providing a flexible body which is inflatable to a first state having an outer shape generally corresponding to said predetermined shape formed in said bone; positioning said flexible body in said cavity having said predetermined shape formed in said bone; inflating said flexible body; and sensing whether said flexible body is inflated to said first state.

In yet another exemplary embodiment of the present disclosure, a system for monitoring wear of orthopedic implant for placement proximate a bearing surface when installed in a body is provided. The system comprising an orthopedic implant body; a plurality of sensors supported by said orthopedic implant body and arranged to be positioned proximate said bearing surface, each sensor corresponding to a location on said orthopedic implant; and an interrogation system to interrogate said plurality of sensors subsequent to installation in said body. Each sensor of said plurality of sensors providing a first indication in response to an interrogation signal in an absence of wear of said orthopedic implant at said location corresponding to said sensor and a second indication in response to said interrogation signal in a presence of wear of said orthopedic implant at said location corresponding to said sensor.

In a yet further exemplary embodiment of the present disclosure, a method of monitoring wear of an orthopedic implant placed proximate a bearing surface when installed in a body is provided. The method comprising the steps of providing a body of said orthopedic implant; providing a plurality of sensors supported by said orthopedic implant body and arranged to be positioned proximate said bearing surface, each sensor corresponding to a location on said orthopedic implant; and interrogating said plurality of sensors to determine if said orthopedic implant has experienced wear.

In still a further exemplary embodiment of the present disclosure, a woven material for use within the body is provided. The woven material comprising a first woven layer having a first plurality of weft fibers and a first plurality of in layer warp fibers, said first layer having a first stiffness; a second woven layer having a second plurality of weft fibers and a second plurality of in layer warp fibers, said second layer having a second stiffness generally less than said first stiffness; a third woven layer having a third plurality of weft fibers and a third plurality of in layer warp fibers, said third layer having a third stiffness generally less than said second stiffness; a first plurality of out of layer warp fibers which couple together said first layer and said second layer; and a second plurality of out of layer warp fibers which couple together said second layer and said third layer.

In still another exemplary embodiment of the present disclosure, an orthopedic implant for positioning proximate a bone in a body is provided. The orthopedic implant comprising a first body portion including a three-dimensional woven material having a plurality of layers; and a second body portion coupled to said three-dimensional woven material. The three-dimensional woven material includes a first woven layer having a first plurality of weft fibers and a first plurality of in layer warp fibers. The first layer having a first stiffness. The orthopedic implant further comprising a second woven layer having a second plurality of weft fibers and a second plurality of in layer warp fibers. The second layer having a second stiffness generally less than said first stiffness. The orthopedic implant further comprising a third woven layer having a third plurality of weft fibers and a third plurality of in layer warp fibers. The third layer having a third stiffness generally less than said second stiffness. The orthopedic implant further comprising a first plurality of out of layer warp fibers which couple together said first layer and said second layer and a second plurality of out of layer warp fibers which couple together said second layer and said third layer.

In still a further exemplary embodiment of the present disclosure, an orthopedic implant for positioning proximate a bone in a body is provided. The orthopedic implant comprising a body portion including a three-dimensional woven material having a plurality of layers; and a plurality of sensors supported by said three-dimensional woven material. The plurality of sensors positioned proximate said bone and configured to provide an indication of a presence of bone ingrowth into said three-dimensional woven material.

In still yet a further exemplary embodiment of the present disclosure, an orthopedic implant for positioning proximate a bone in a body. The orthopedic implant comprising a body portion including a three-dimensional woven material having a plurality of layers; and sensing means supported by said three-dimensional woven material, said sensing means being passive.

In still yet another exemplary embodiment of the present disclosure, a method of measuring bone in-growth into an orthopedic implant placed proximate a bone when installed in a body is provided. The method comprising the steps of providing a body of said orthopedic implant, said body including a woven material; providing a sensor supported by said woven material and arranged to be positioned proximate said bone; and interrogating said sensor to determine if said bone has grown into said woven material, said sensor providing a first indication if bone in-growth is present.

In another exemplary embodiment of the present disclosure, a method of measuring strain experienced by an orthopedic implant placed proximate a bone when installed in a body is provided. The method comprising the steps of providing a body of said orthopedic implant, said body including a woven material; providing a sensor supported by said woven material and arranged to be positioned proximate said bone; and interrogating said sensor to determine an amount of strain experienced by said orthopedic implant.

In still another exemplary embodiment of the present disclosure, an assembly is provided. The assembly comprising a flexible body having a folded state and an unfolded state; and a plurality of sensors supported by said flexible body. The plurality of sensors providing an indication of whether said flexible body is in said folded state or said unfolded state.

In yet another exemplary embodiment of the present disclosure, an assembly is provided. The assembly comprising a flexible body having a folded state and an unfolded state; and means for sensing whether said flexible body is in said folded state or said unfolded state.

Additional features and advantages of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The detailed description of the drawings particularly refers to the accompanying figures in which:

FIG. 14 is a representation of a resonant circuit which may be supported by an orthopedic implant as a sensor;

FIG. 15 is a representation of a circuit which may be supported by an orthopedic implant as a sensor;

FIG. 16 is a representation of the circuit of FIG. 15 including a power source;

FIG. 17 is a representation of the resonant circuit of FIG. 14 wherein an antenna of the resonant circuit is wrapped around a fiber of a woven material of an orthopedic implant;

DETAILED DESCRIPTION OF THE DRAWINGS

The embodiments of the invention described herein are not intended to be exhaustive or to limit the invention to the precise forms disclosed. Rather, the embodiments selected for description have been chosen to enable one skilled in the art to practice the invention.

The present disclosure includes multiple uses of sensors in combination with orthopedic implants. Many types of orthopedic implants are known. Exemplary implants include implants to replace a portion of a hip joint and implants to replace portions of a knee joint. As used herein the term orthopedic implant is defined as a device for installation in a living body to provide structural support to at least a portion of the living body.

Exemplary orthopedic implants for a hip joint, specifically hip stems and acetabular cups are provided in U.S. patent application Ser. No. 11/687,862, filed Mar. 19, 2007, assigned to the assignee of the present application. Exemplary surgical techniques to install hip stems and acetabular cups are described in U.S. Pat. No. 6,676,706, issued Jan. 13, 2004; U.S. Pat. No. 6,860,903, issued Mar. 1, 2005; U.S. Pat. No. 6,953,480, issued Oct. 11, 2005; U.S. Pat. No. 6,991,656, issued Jan. 31, 2006; abandoned U.S. patent application Ser. No. 10/929,736, filed Aug. 30, 2004; U.S. patent application Ser. No. 10/952,301, filed Sep. 28, 2004; U.S. patent application Ser. No. 11/235,286, filed Sep. 26, 2005; and U.S. patent application Ser. No. 11/105,080, filed Apr. 13, 2005, all titled METHOD AND APPARATUS FOR PERFORMING A MINIMALLY INVASIVE TOTAL HIP ARTHROPLASTY, all assigned to the assignee of the present application, the disclosures of which are hereby expressly incorporated herein by reference.

Figures 1, 2:
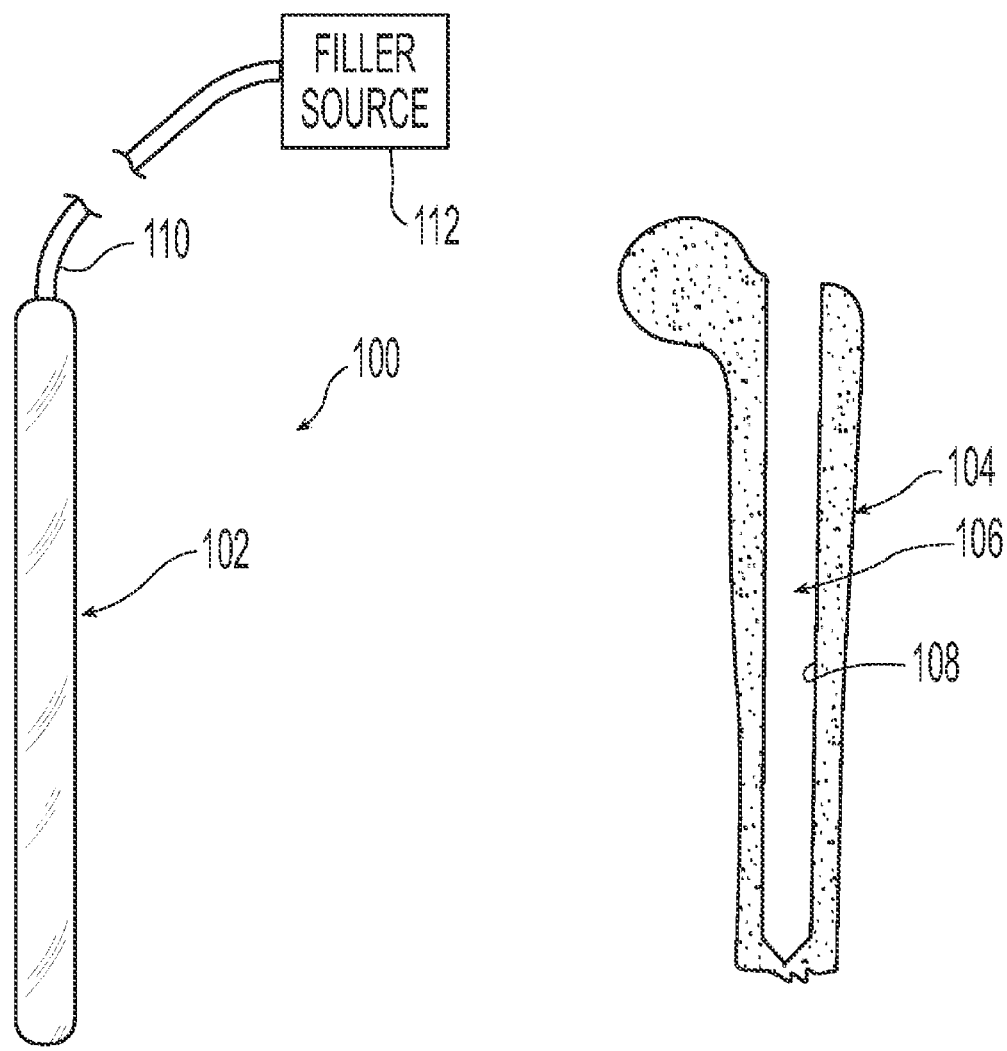
FIG. 1 illustrates an inflatable orthopedic implant connected to a filler source.
FIG. 2 illustrates a bone having a cavity bored therein.

One type of orthopedic implant is an inflatable orthopedic implant 100. Referring to FIG. 1, inflatable orthopedic implant 100 includes a flexible body 102. Flexible body 102 is sized to be placed in a cavity 106 formed in a bone 104. Cavity 106 is generally created during a surgical procedure by boring and/or other operations to remove bone material from bone 104. Cavity 106 has a predetermined shape 108.

Flexible body 102 has an uninflated state and an inflated state. In the uninflated stated, flexible body 102 has an outer envelope smaller than the envelope of flexible body 102 in the inflated state. Flexible body 102 is inflated by introducing a filler material 113 (see FIG. 4) from a filler source 112 through a conduit 110 into an interior of flexible body 102. In one embodiment, the filler material 113 being under pressure to force it through conduit 110 and into flexible body 102. In one embodiment, the filler material 113 is an expandable material which is placed in flexible body 102 and subsequently expands to cause flexible body 102 to inflate. An exemplary filler material 113 is bone cement. The envelope of flexible body 102 in the inflated state generally corresponds to the shape 108 of cavity 106 in bone 104. An exemplary inflatable orthopedic implant 100' having a flexible body 102' shaped for use as a portion of a hip stem is provided in FIGS. 8, 9A, and 9B. Additional details regarding exemplary inflatable implants are provided in U.S. Pat. No. 6,425,923, issued Jul. 30, 2002, titled CONTOURABLE POLYMER FILLED IMPLANT, assigned to the assignee of the present disclosure, the disclosure of which is expressly incorporated by reference herein.

Figure 3:
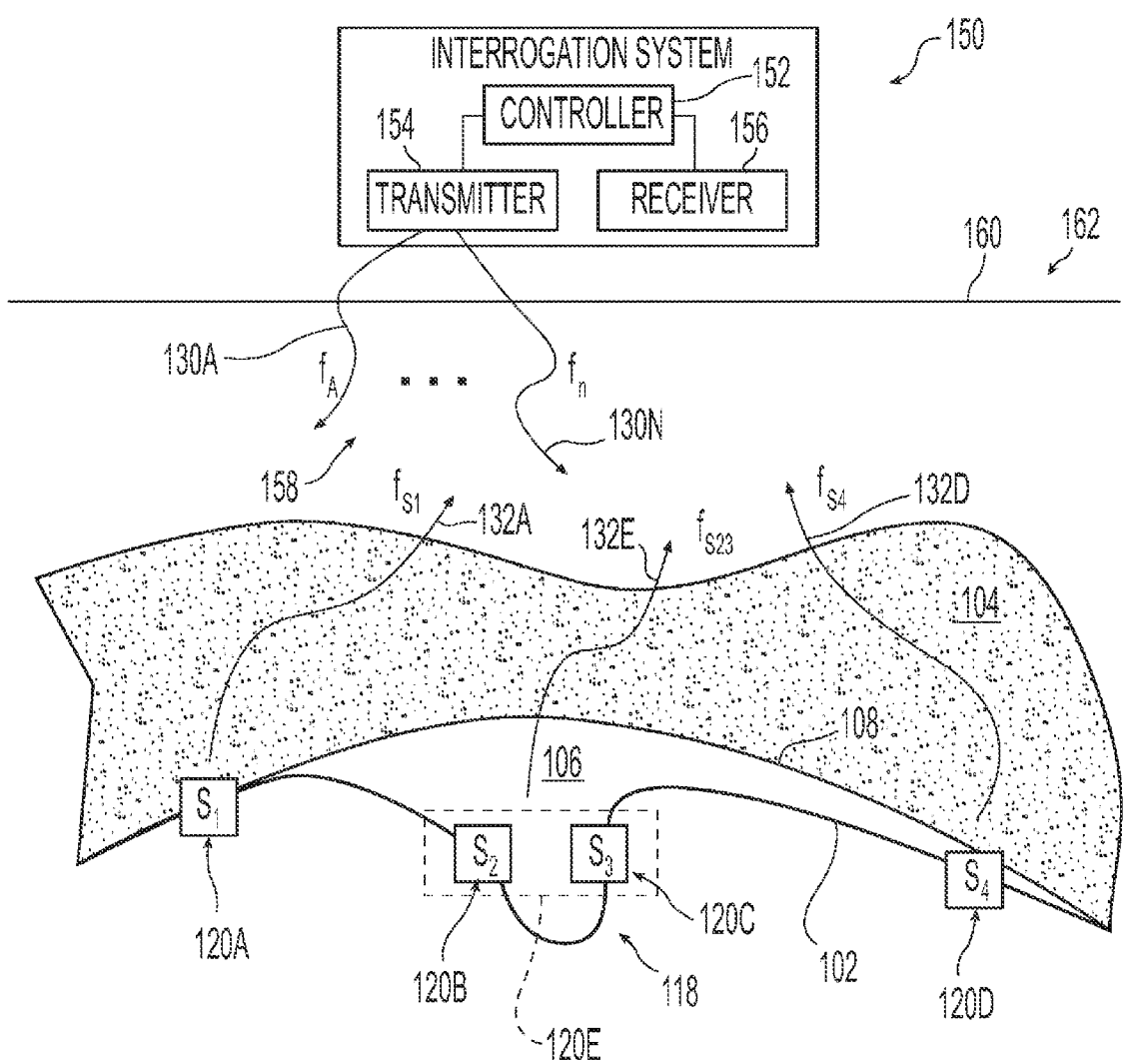
FIG. 3 illustrates a portion of the inflatable implant of FIG. 1 inserted into the cavity of FIG. 2, the inflatable implant having a fold and including a plurality of sensors supported by the inflatable implant which may be interrogated by an external device.
Figure 4:
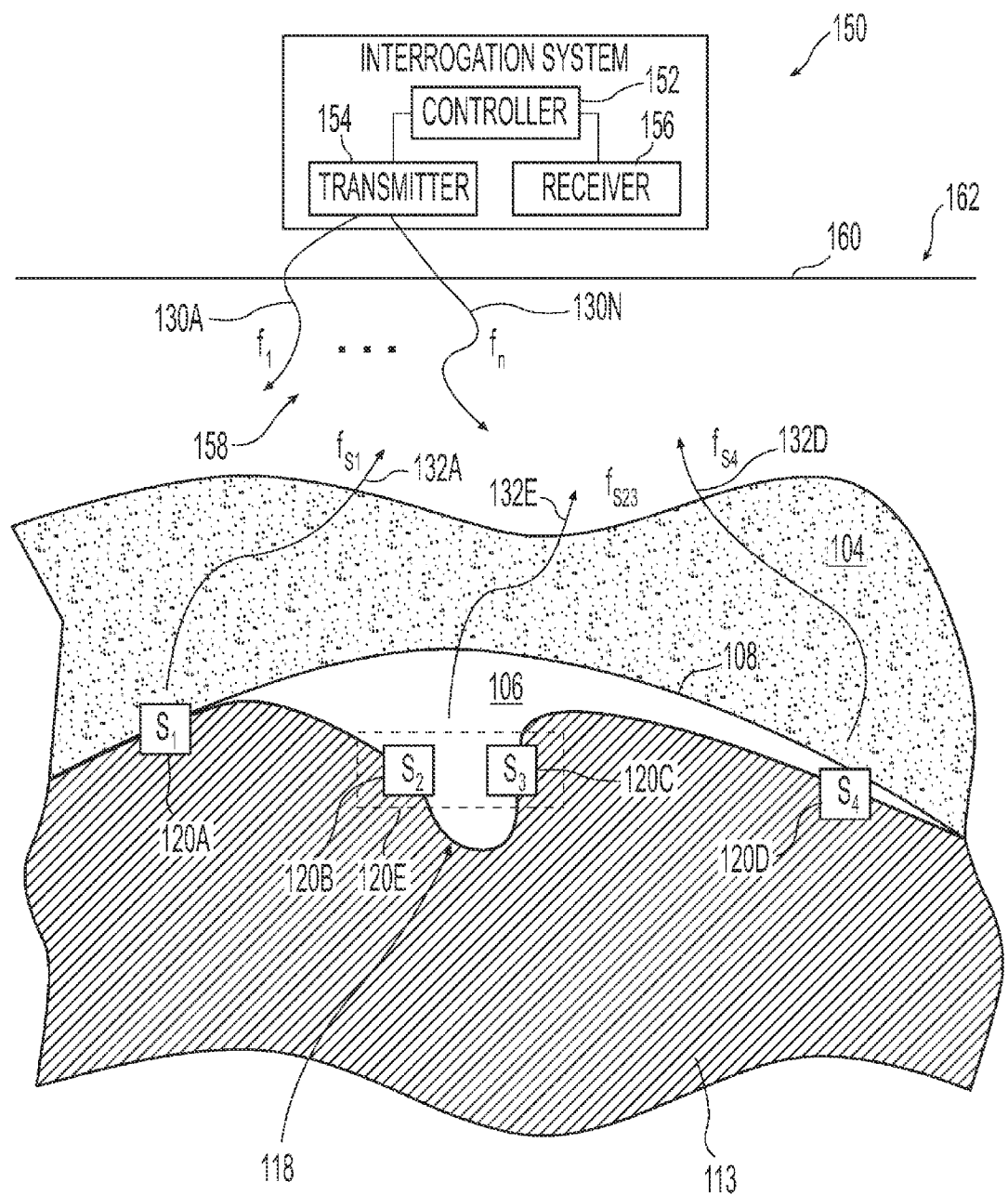
FIG. 4 illustrates the inflatable implant of FIG. 3 with a filler material placed therein.
Figure 5:
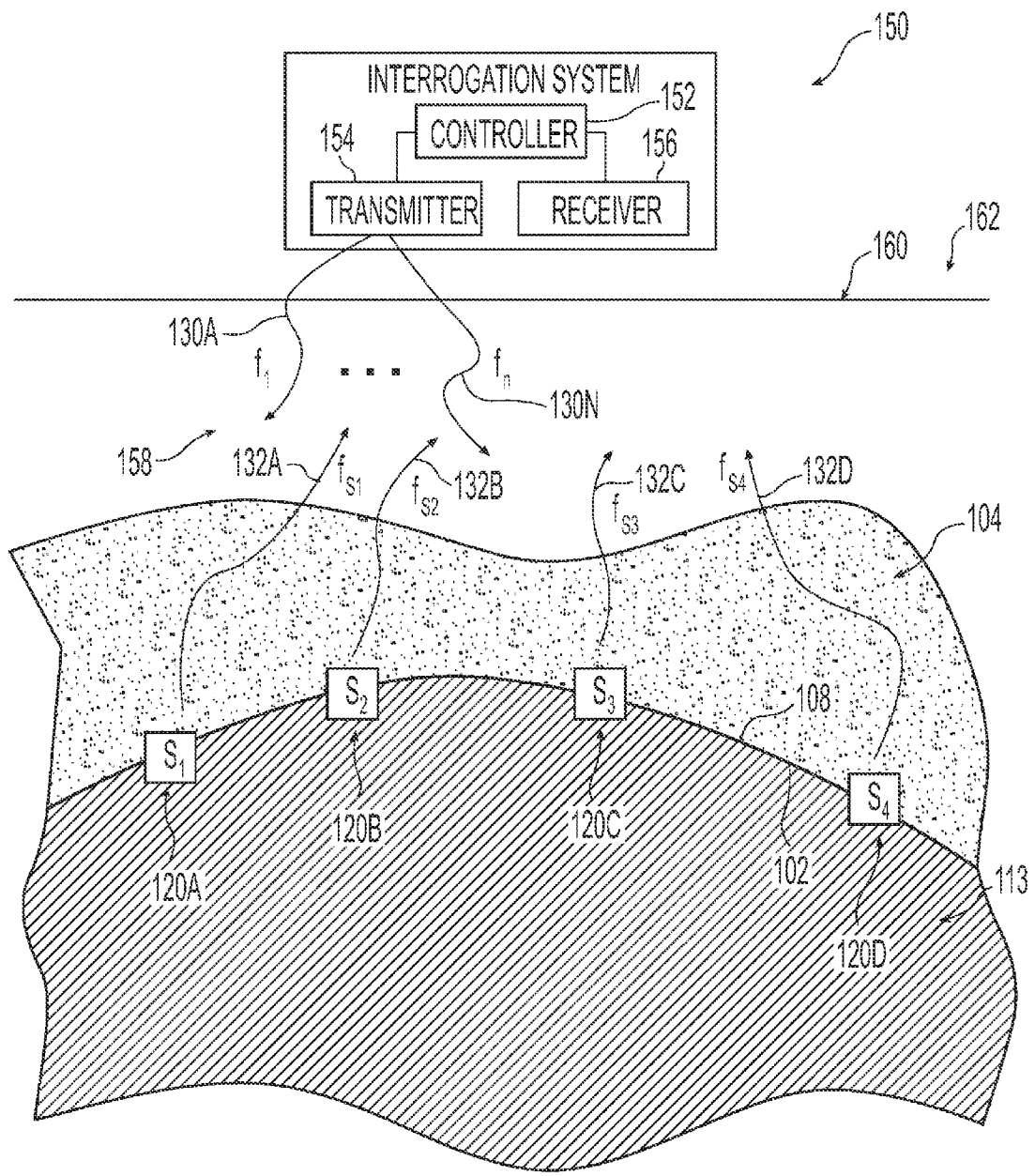
FIG. 5 illustrates the inflatable implant of FIG. 4 having additional filler material placed therein, the inflatable implant being fully inflated.

Referring to FIG. 3, a representation of a portion of flexible body 102 placed in cavity 106 of bone 104 is shown. Flexible body 102 includes a fold 118 and is in the uninflated state because its shape does not generally correspond to shape 108 of cavity 106. Referring to FIG. 4, flexible body 102 has been filled with filler material 113. However, fold 118 is still present. Referring to FIG. 5, additional filler material 113 has been added causing the expansion of flexible body 102 and the removal of fold 118. In FIG. 5, the shape of flexible body 102 generally matches shape 108 of cavity 106. In one embodiment, flexible body 102 has a shape other than the shape of cavity 106 when in the inflated state.

As shown in FIGS. 3-5, flexible body 102 further supports a plurality of sensors 120A-D which are used to determine whether flexible body is in the fully inflated state of FIG. 5, or a non-inflated state, such as in FIGS. 3 and 4. Although four sensors 120A-D are represented, flexible body 102 may include any number of sensors. Sensors 120 are included to detect the presence of fold 118 in flexible body 102. In one embodiment, sensors 120 are passive sensors which receive an excitation energy from an external source. In one embodiment, sensors 120 are active sensors having a power source coupled thereto.

In one embodiment, sensors 120 are resonant circuits 122 which emit a signal of a respective frequency in response to receiving an excitation or interrogation signal of given frequency. The operation of resonant circuits 122 are well known. Referring to FIG. 14, a representation of a resonant circuit 122 is shown. Resonant circuit 122 includes an antenna 124 which receives an interrogation signal 130 having a first frequency and emits in response thereto a response signal 132 having a second frequency. In one embodiment, the second frequency of the response signal 132 is the same as the first frequency of the excitation signal. Resonant circuit 122 includes a capacitive element 126 and a resistive element 128. In one embodiment, capacitive element 126 is comprised of multiple layers surrounding a fiber of a woven material. Resistive element 128 is shown to represent the parasitic resistance in the circuit. However, in one embodiment, a resistive element, such as a resistor, may be included to limit the frequency range of circuit 122 or shift the frequency of the response signal 132. Also, in one embodiment resistive element 128 may function as a sensor. The expected second frequency (such as equal to the first frequency) may be altered by changes in the amount of resistance in the circuit or the duration of the response signal may be altered. Changes in resistance may indicate a change in the tissue in contact with circuit 122 or a strain or other force experienced by circuit 122.

Returning to FIG. 4, an interrogation system 150 is represented. Interrogation system 150 includes a controller 152, a transmitter 154, and a receiver 156. Controller 152 includes a frequency sweep generator and causes transmitter 154 to emit a plurality of discrete interrogation signals 130A-130N across a frequency spectrum 158 ($f_A$ to $f_N$). These interrogation signals 130 pass through the skin or tissue 160 of a living body 162.

Each of sensors 120A-D is tuned to a respective interrogation frequency included in frequency spectrum 158. Each of sensors 120A-D provides a respective response signal 132 at a discrete frequency in response to receiving the respective interrogation signal. These response signals 132 pass through the skin or tissue 160 of a living body 162. In one embodiment, the frequency of interrogation signals and response signals are generally around about 120 kHz. In one embodiment, the frequency of interrogation signals and response signals are generally in a range of about 120 kHz to less than 1 GHz. In one embodiment, the frequency of interrogation signals and response signals are generally in a range of about 120 kHz to less than 400 MHz.

Turning to FIG. 5, flexible body 102 is in the inflated state and its shape generally matches shape 108 of cavity 106. In the inflated state, sensors 120A-D are spaced apart such that each responds to interrogation device 150 separately. In response to an interrogation signal 130A at a first frequency, sensor 120A emits a response signal 132A at generally the first frequency. In response to an interrogation signal 130B at a second frequency, sensor 120B emits a response signal 132B at generally the second frequency. In response to an interrogation signal 130C at a third frequency, sensor 120C emits a response signal 132C at generally the third frequency. In response to an interrogation signal 130D at a fourth frequency, sensor 120D emits a response signal 132D at generally the fourth frequency. If all four of the response signal 132A, response signal 132B, response signal 132C, and response signal 132D are received by receiver 156 in response to the first frequency (interrogation signal 130A), the second frequency (interrogation signal 130A), the third frequency (interrogation signal 130A), and the fourth frequency (interrogation signal 130A), respectively, controller 152 determines that fold 118 is not present and at least that portion of flexible body 102 is fully inflated. An active element may be used to change the response frequency or modulate the response signal, such as to include identification data. With a SAW ("a passive element" like an echo chamber) a modulated signal, such as one including identification data, may be created without an active control element.

Returning to FIG. 4, if fold 118 in flexible body 102 is still present then sensors 120B and 120C do not behave as described above. The two inductors (antennas) of sensors 120B and 120C begin to affect one another (mutual inductance). The resonant response of the individual sensors 120B and 120C begins to decline, and the response of the combined circuit begins to increase. When the two (or more) sensors are very close (due to their closer proximity because of fold 118 in flexible body 102), the sensors act as a single sensor. As shown in FIG. 4, sensors 120B and 120C act as a single sensor and provide a response signal 132E at a fifth frequency instead of the two response signals, response signals 132B and 132C, at the second frequency and the third frequency. As such, if the fifth frequency (response signal 132E) is received by receiver 156 or if one or both of the second frequency (response signal 132B) and the third frequency (response signal 132C) are not received by receiver 156, then controller 152 determines that fold 118 is present in flexible body 102 and at least that portion of flexible body 102 is not fully inflated. Further, if controller 152 determines that the received signal at the second frequency (response signal 132B) and the third frequency (response signal 132C) are not at an amplitude above a threshold (due to the mutual inductance) then controller 152 may determine that fold 118 is present.

In one embodiment, inflatable implant 100 is inserted into cavity 106 formed in bone 104. Filler material 113 is provided to an interior of flexible body 102. As filler material is being provided to the interior of flexible body 102 or at discrete stop times during the filling of flexible body 102 with filler material 113, interrogation system 150 interrogates resonant circuits 122 to determine if flexible body 102 is fully inflated. As discussed above, if all of the respective resonant circuits are providing their unique response signal 132 than flexible body 102 is fully inflated. In one embodiment, the location of each resonant circuit 122 is mapped to its location on flexible body 102. As such, by knowing which resonant circuits 122 are not providing their unique response signal 132, an operator or a software application may determine the portion of flexible body 102 which is not fully inflated.

Although flexible body 102 is described herein in connection with orthopedic implants, flexible body may be any component which may include a fold. Another exemplary flexible body is a parachute. When flexible body 102 is a parachute, sensors 120 may be used to provide an indication whether the parachute is properly folded or not based on the relative position of sensors 120.

In one embodiment, sensors 120A-D are optical sensors. In one embodiment, sensors 120A-D are diffraction gratings provided at discrete locations along an optical fiber 166 which is coupled to or forms a part of flexible body 102. As is known, the shape 168 of optical fiber 166 may be determined by an optical controller 170 based on the analysis of light interaction with the diffraction gratings. This shape sensing technology is available from Luna Innovations located at 1 Riverside Circle, Suite 400, Roanoke, Va. 24016. Additional details regarding an exemplary optical system including diffraction gratings and the methods to determine a shape of the optical system are disclosed in U.S. Published patent application Ser. No. 11/535,438, filed Sep. 26, 2006, titled FIBER OPTIC POSITION AND SHAPE SENSING DEVICE AND METHOD RELATING THERETO, assigned to Luna Innovations Incorporated, the disclosure of which is expressly incorporated by reference herein.

Figure 6:
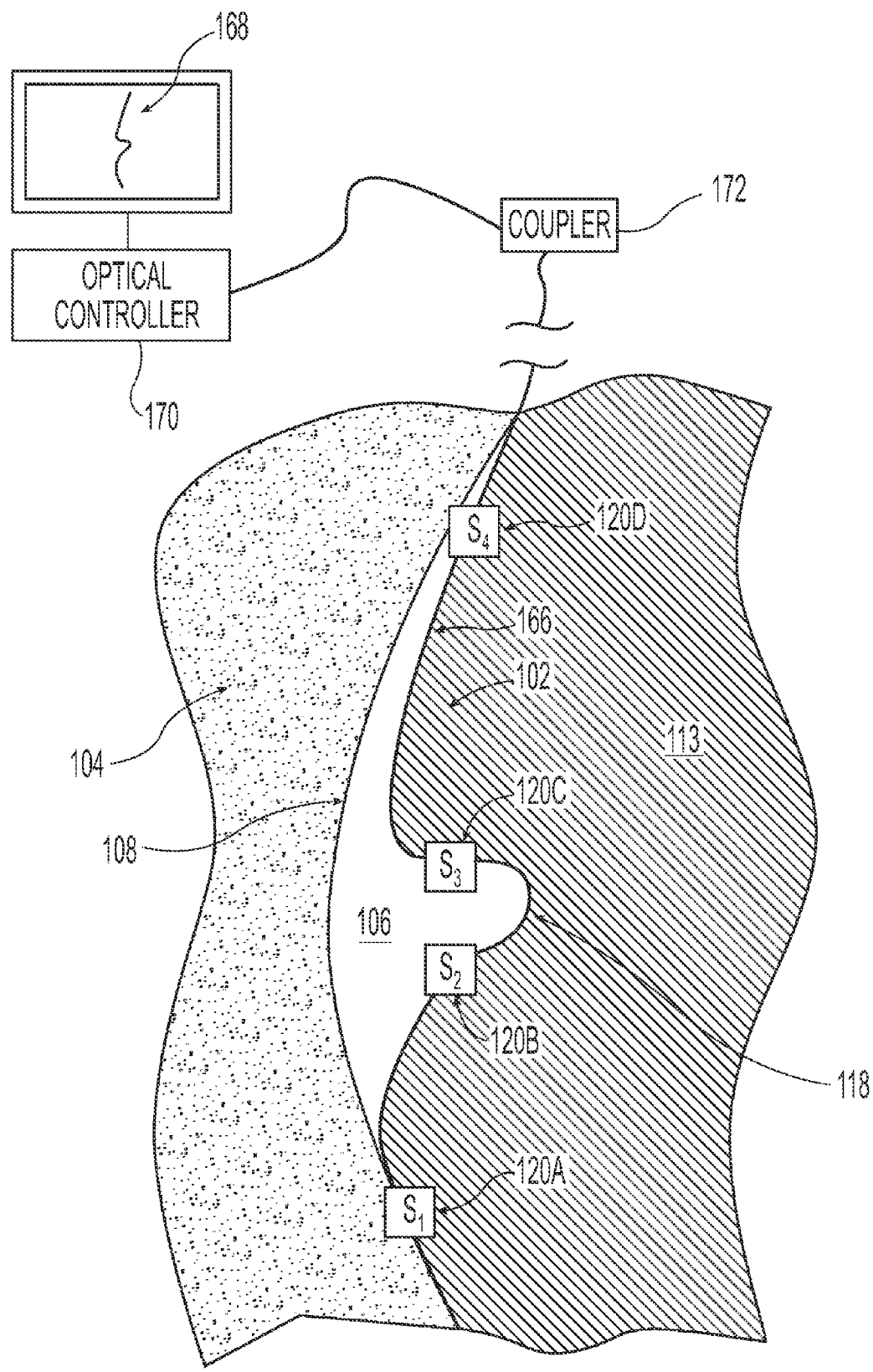
FIG. 6 illustrates a portion of the inflatable implant of FIG. 1 inserted into the cavity of FIG. 2, the inflatable implant having a fold and including a plurality of optical sensors supported by the inflatable implant.
Figure 7:
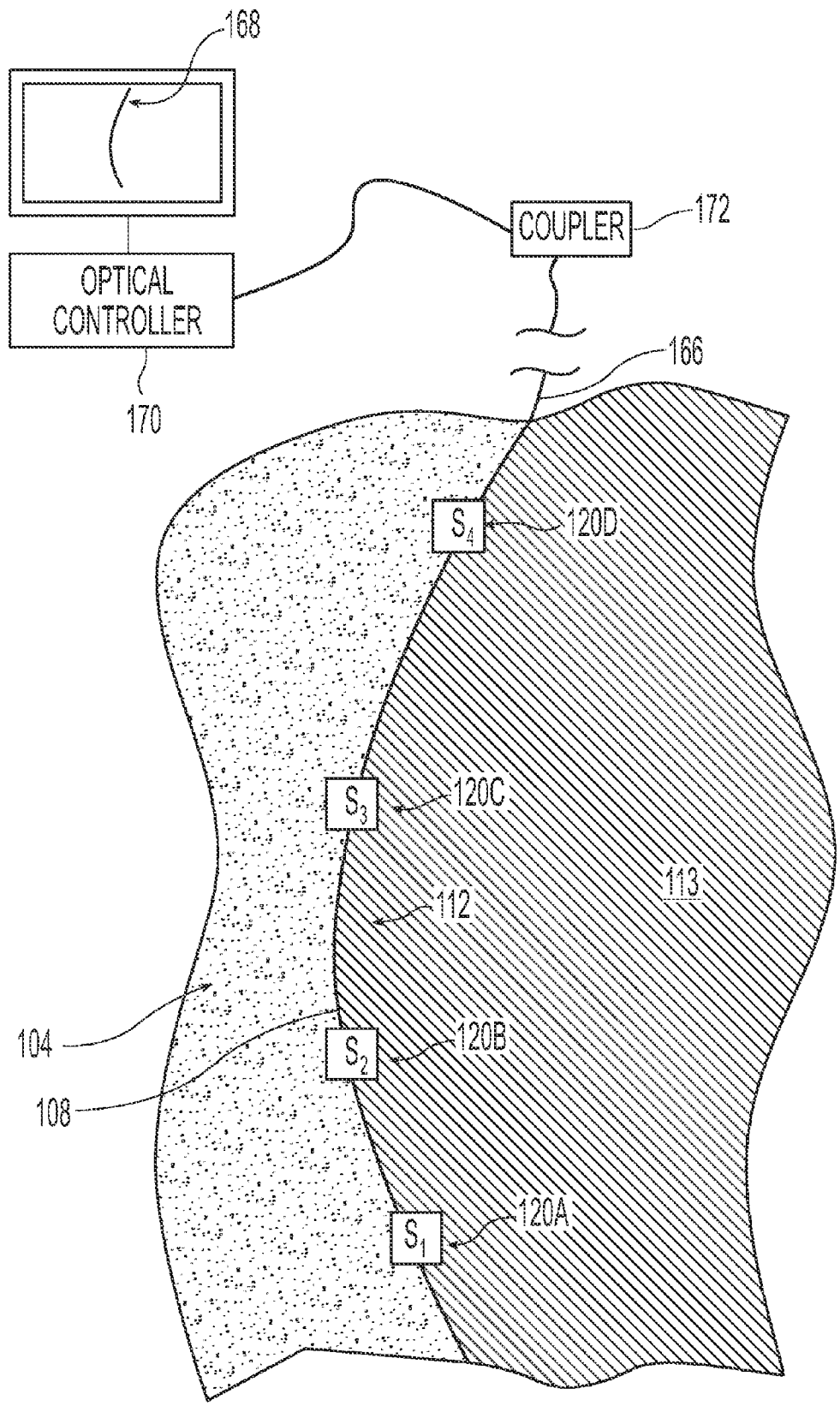
FIG. 7 illustrates the inflatable implant of FIG. 6 having additional filler material placed therein, the inflatable implant being fully inflated.

As shown in FIG. 6, the shape 168 of optical fiber 166 includes fold 118 of flexible body 102. The fold is shown on the display which provides an indication of the shape of the optical fiber 166. As such, an operator or a software application may determine that flexible body 102 is not fully inflated based on the shape of the optical fiber. Referring to FIG. 7, the shape 168 of optical fiber 166 does not include fold 118 of flexible body 102. The fold is not shown on the display which provides an indication of the shape of the optical fiber 166. As such, an operator or a software application may determine that flexible body 102 is fully inflated based on the shape of the optical fiber.

In one embodiment, inflatable implant 100 is inserted into cavity 106 formed in bone 104. Optical controller 170 is coupled to the one or more optical fibers through a coupler 172 to provide one or more interrogation optical signal that interacts with the diffraction gratings in optical fiber 166 and to receive one or more response optical signals back from optical fiber 166 which are used to determine the shape 168 of optical fiber 166. Filler material 113 is provided to an interior of flexible body 102. As filler material is being provided to the interior of flexible body 102 or at discrete stop times during the filling of flexible body 102 with filler material 113, the shape 168 of the one or more optical fibers 166 is determined. The shape 168 of the optical fiber 166 provides the shape of flexible body 102 and thus an indication of whether flexible body 102 is fully inflated or not. Once flexible body 102 is fully inflated, optical controller 168 is uncoupled from the installed implant 100.

Figure 8:
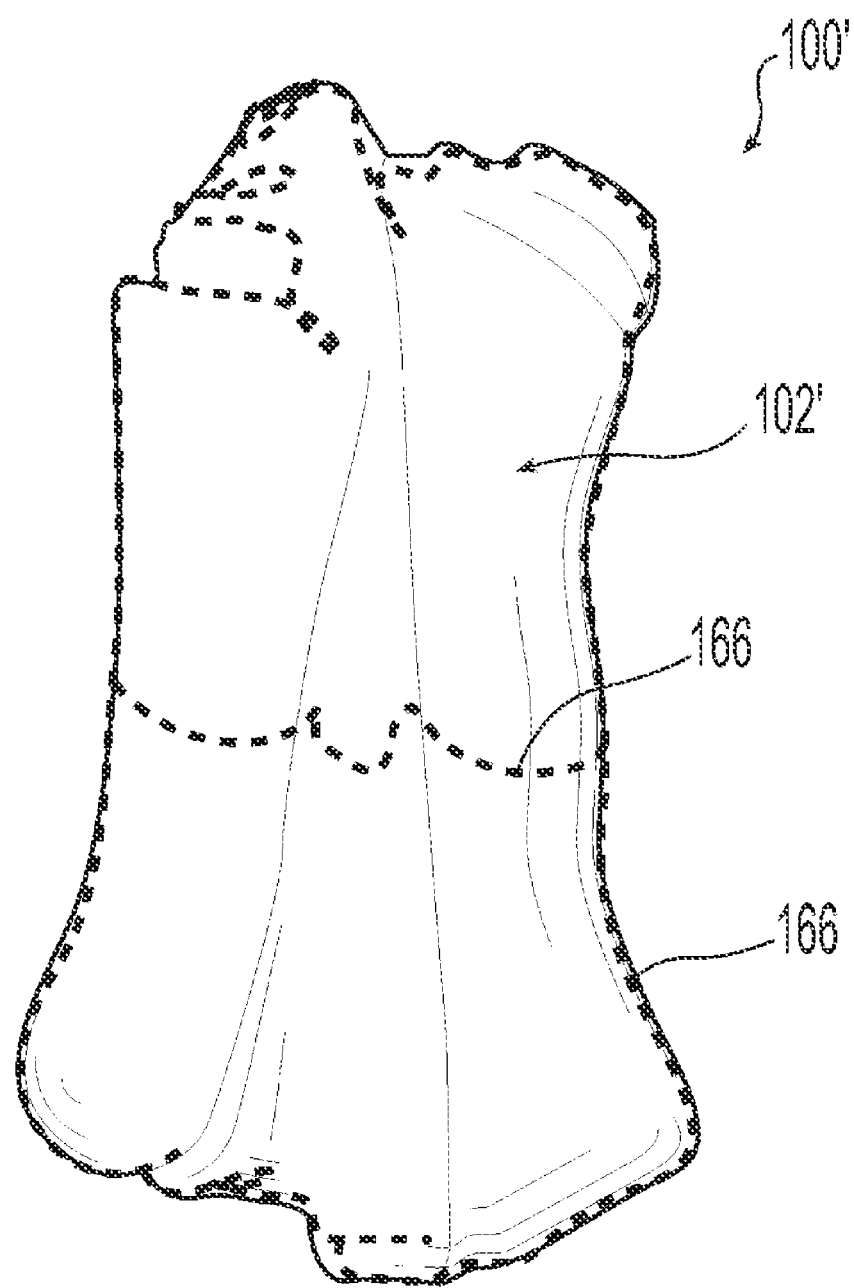
FIG. 8 is an exemplary embodiment of an inflatable implant for a hip stem having optical sensors, the inflatable implant being in a non-inflated state.
Figure 9B:
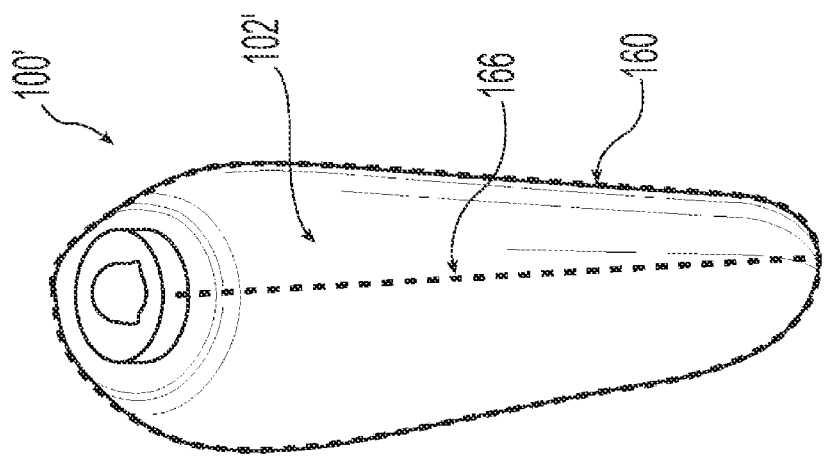
FIG. 9B is a side view of the inflatable implant of FIG. 8 fully inflated.
Figure 9A:
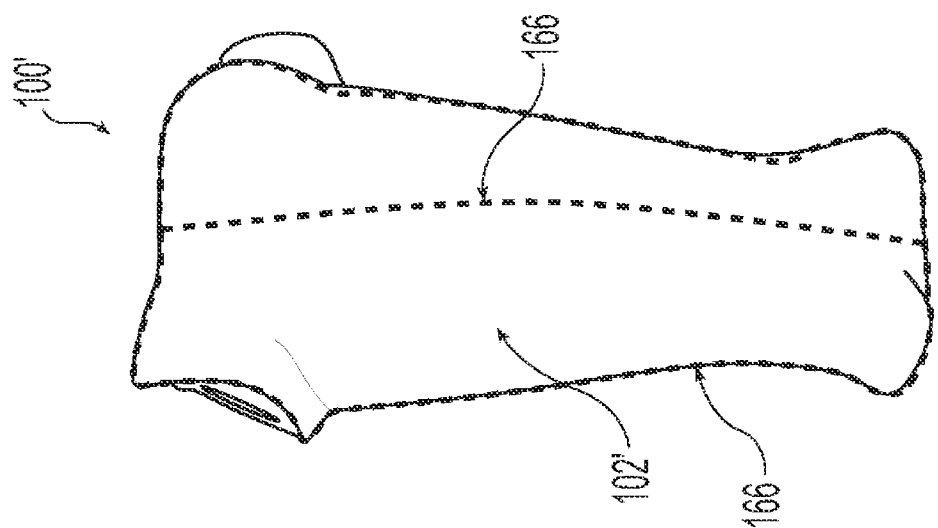
FIG. 9A is a front view of the inflatable implant of FIG. 8 fully inflated.

Referring to FIG. 8, an exemplary embodiment of an inflatable implant 100' including a flexible body 102' in a non-inflated state is shown. The positions of one or more optical fibers 166 are illustrated by dashed lines. Referring to FIGS. 9A and 9B, the same embodiment of flexible body 102' is shown in a fully inflated state. Again, the positions of the one or more optical fibers 166 are illustrated by dashed lines. It is this layout of optical fibers 166 that an operator or software application would recognize as an indication that flexible body 102 is in the fully inflated state.

Returning to FIGS. 8, 9A, and 9B, in one embodiment the optical fibers 166 are replaced with one or more fibers which are marginally conductive. The resistively of the fibers are monitored. In one embodiment, the conductivity of the fibers is at a first value when implant 100 is fully inflated. In one embodiment, the first value is a minimum value.

Figure 10:
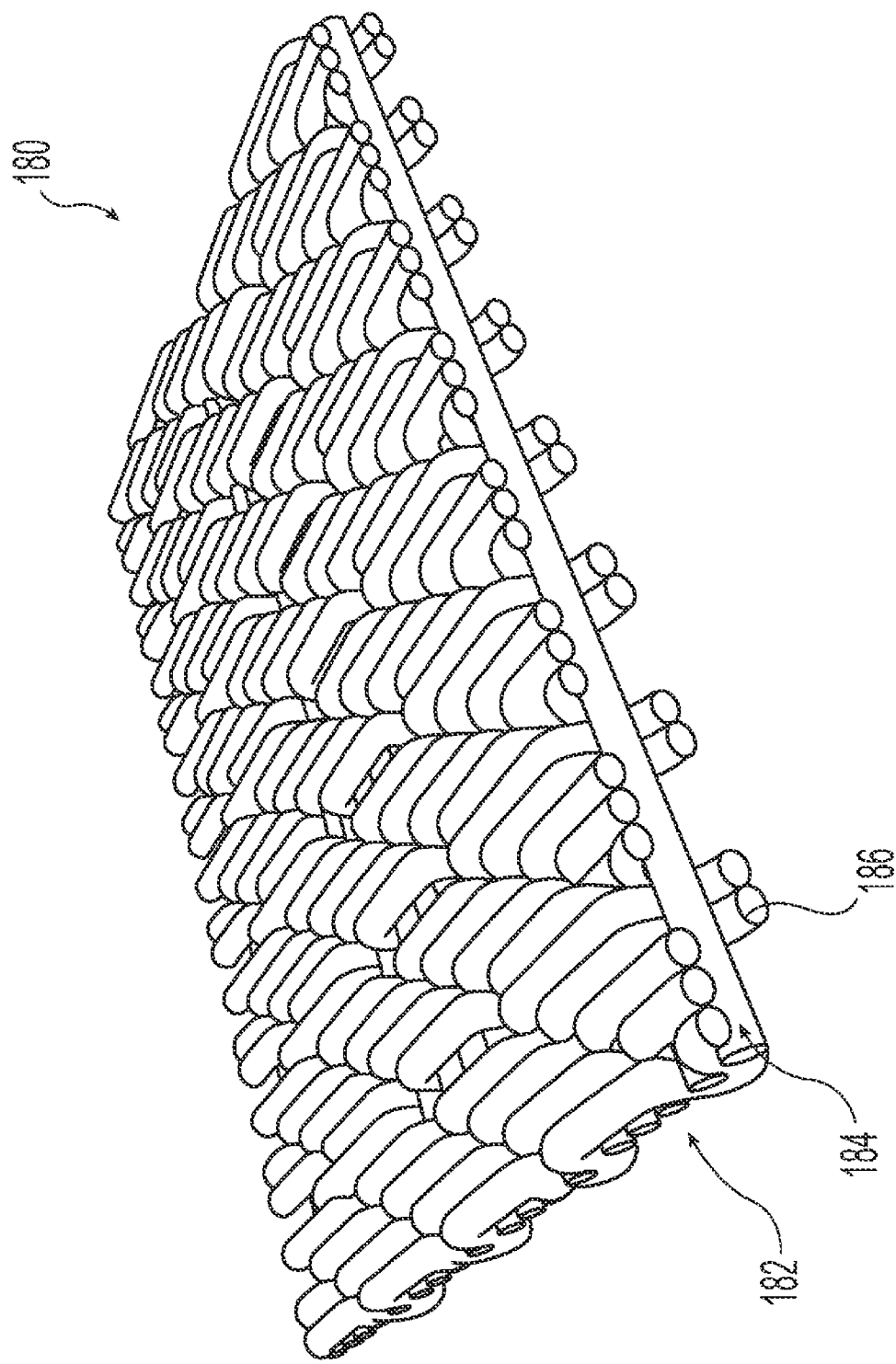
FIG. 10 is a representation of a single layer woven material having a plurality of weft fibers and a plurality of warp fibers, each warp fiber floating over a plurality of weft fibers.

In one embodiment, flexible body 102' is made of a woven material 180. Referring to FIG. 10, woven material 180 includes a single layer fabric 182 including a plurality of weft fibers 184 and a plurality of warp fibers 186. Optical fibers 166 may replace one of weft fibers 182 and warp fibers 184 and form part of woven material 180. As illustrated warp fibers 186 are floated over four weft fiber 184 to reduce the amount of bending of optical fibers 166. The warp fibers 186 which correspond to optical fibers 166 may be floated over more or less weft fibers 184. In one embodiment, the warp fibers 186 which correspond to optical fibers 166 are floated over at least two of the weft fibers 184.

Woven material 180 may be made from any type of biocompatible material which results in a flexible body having a non-inflated state and an inflated state. Exemplary materials include polymers, such as thermoplastics and hydrophilic hydrogels; bio-degradable materials; acrylics; natural fibers; metals; glass fibers; carbon fibers; ceramics; and other suitable materials. Exemplary polymers include propylene, polyester, high density polyethylene (HDPE), low density polyethylene (LDPE), ultra-high molecular weight polyethylene (UHMWPE), polycarbonate urethane, polyetheretherketones (PEEK). Exemplary hydrophilic hydrogel include polyvinyl alcohol (PVA), polyvinylpyrrolidone (PVP), and polyethylene glycol (PEG). Exemplary bio-degradable materials include Polylactic Acid (PLA), poly-L-lactide (PLLA) and polyglycolic acid (PGA). Exemplary acrylics include polymethyl methacrylate (PMMA). Exemplary natural fibers include elasin, keratin, silk, hydroxyl apatite (HA), collagen, and chitosan. Exemplary metals include stainless steel, titanium, titanium alloys, cobalt, nickel titanium alloy (nitinol), and tantalum. Exemplary ceramics include zirconia, alumina, and silica.

Figure 11:
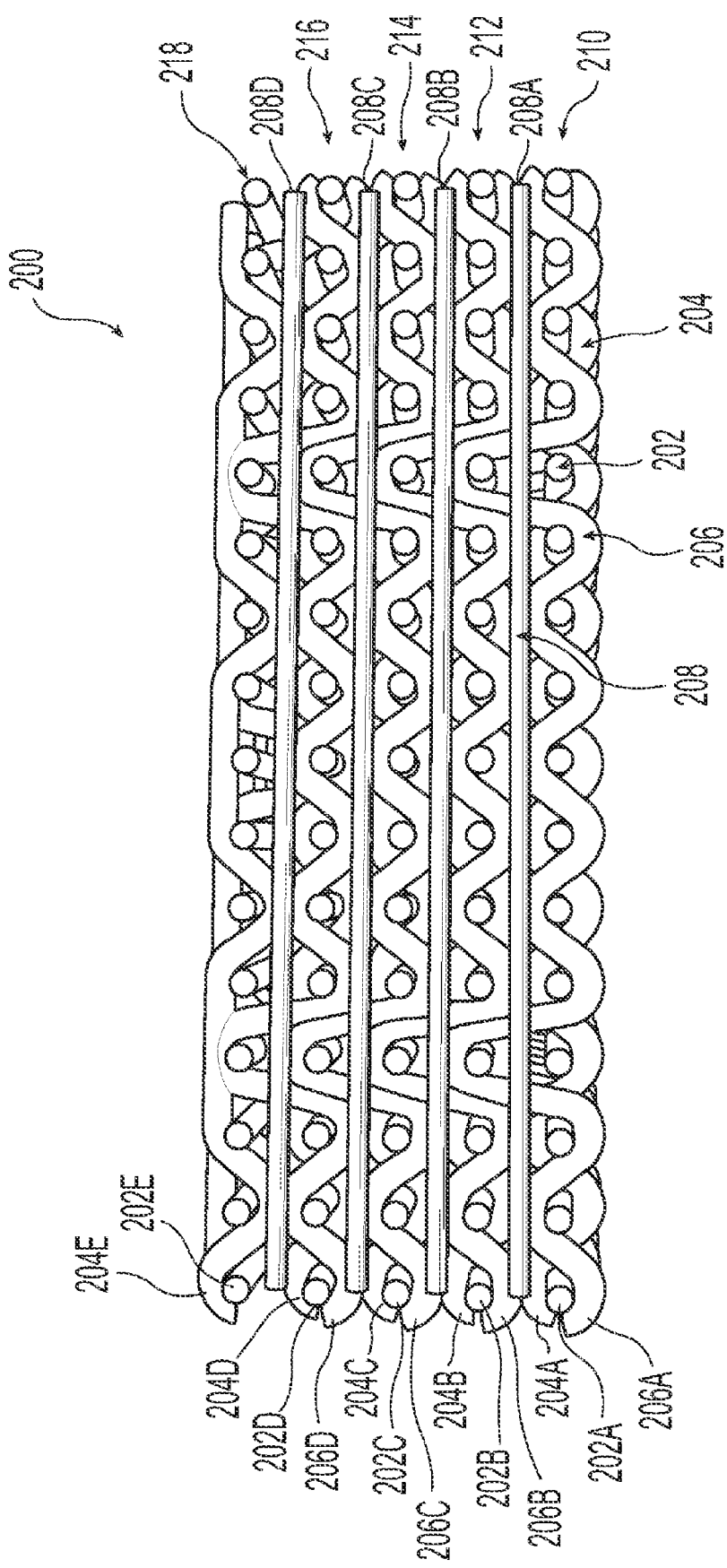
FIG. 11 is a representation of a multi-layer three-dimensional woven material including a plurality of weft fibers, a plurality of in layer warp fibers, a plurality of out of layer warp fibers, and a plurality of straight warp fibers.
Figure 12:
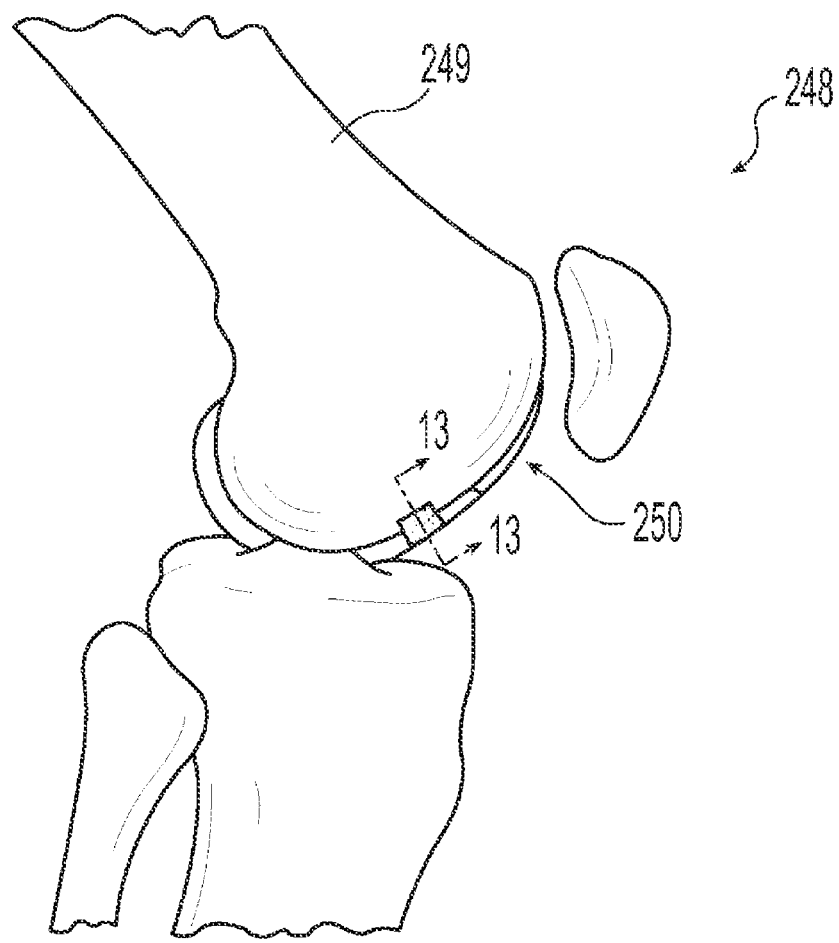
FIG. 12 is a representation of the bones of a knee joint and an orthopedic implant coupled to a femur bone.
Figure 13:
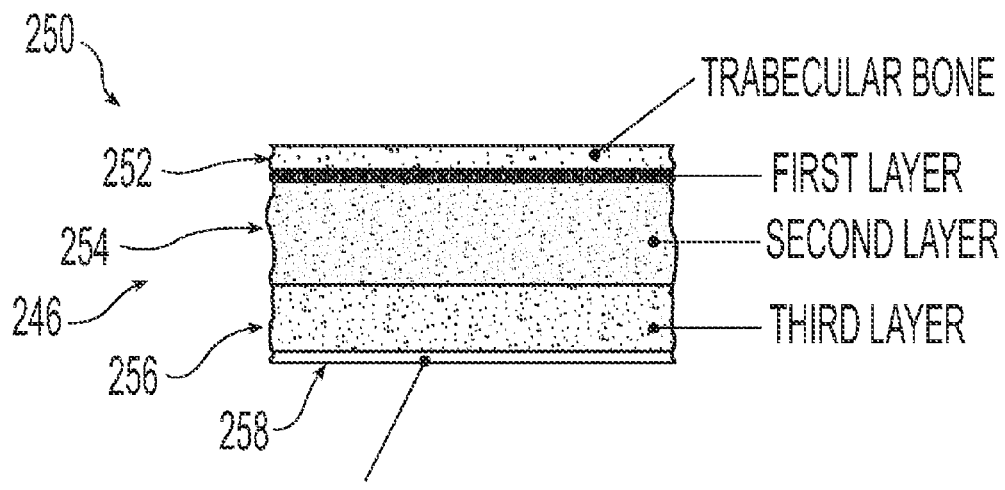
FIG. 13 is a representative cross-section of the orthopedic implant of FIG. 12.
Figure 18:
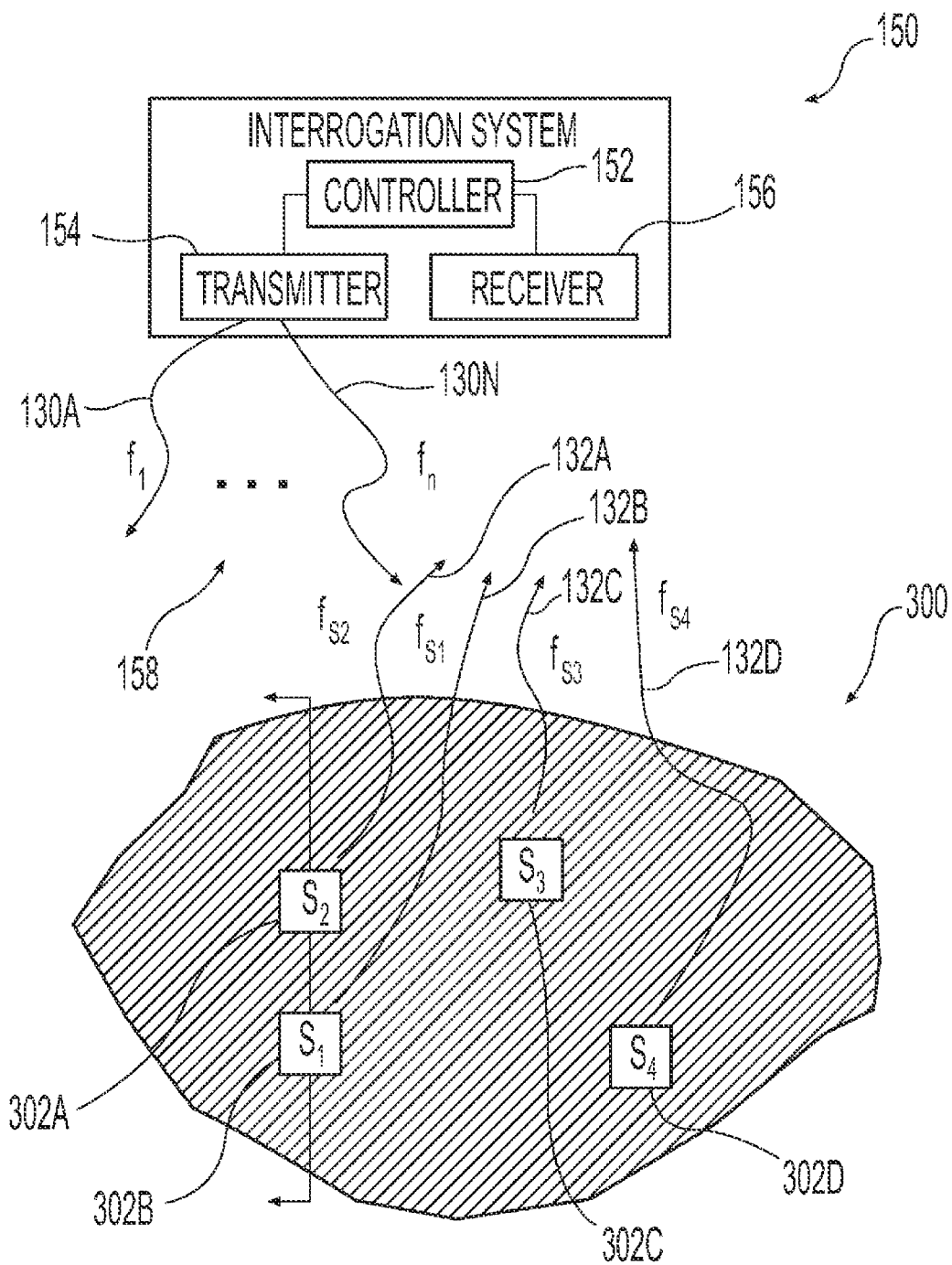
FIG. 18 is a representation of an end view of an orthopedic implant having a plurality of sensors, each sensor corresponding to a location.

Further, inflatable implant 100' may be made from a three-dimensional woven material 200. Referring to FIG. 11, three-dimensional woven material 200 is shown. In one embodiment, three-dimensional woven material 200 includes fibers which make a generally rigid body for use as an orthopedic implant. In one embodiment, three-dimensional woven material 200 includes fibers which make a generally flexible body 102 for an inflatable orthopedic implant 100.

Referring to FIG. 11, a portion of a three-dimensional woven material 200 is shown. Three-dimensional woven material 200 includes a plurality of weft fibers 202 (extending out of the page), a plurality of in layer warp fibers 204, and a plurality of out of layer warp fibers 206. In the illustrated embodiment, three-dimensional woven material 200 also includes a plurality of straight warp fibers 208.

In the illustrated embodiment, three-dimensional woven material 200 includes five layers 210, 212, 214, 216, and 218. Each of the layers 210, 212, 214, 216, and 218 is coupled to the adjacent layers through the out of layer warp fibers 206. Although five layers are shown, three-dimensional woven material 200 may include between two and five layers or more than five layers. Further, although out of layer warp fibers 206 are shown coupling two adjacent layers together, the out of layer warp fibers 206 may couple more than two layers together.

Each of weft fibers 202, in layer warp fibers 204, out of layer warp fibers 206, and straight warp fibers 208 may be made of one or more materials. In the case of multiple materials, the respective fiber may be a braided fiber. Exemplary materials include polymers, such as thermoplastics and hydrophilic hydrogels; biodegradable materials; acrylics; natural fibers; metals; glass fibers; carbon fibers; ceramics; and other suitable materials. Exemplary polymers include propylene, polyester, high density polyethylene (HDPE), low density polyethylene (LDPE), ultra-high molecular weight polyethylene (UHMWPE), polycarbonate urethane, polyetheretherketones (PEEK). Exemplary hydrophilic hydrogel include polyvinyl alcohol (PVA), polyvinylpyrrolidone (PVP), and polyethylene glycol (PEG). Exemplary bio-degradable materials include Polylactic Acid (PLA), poly-L-lactide (PLLA) and polyglycolic acid (PGA). Exemplary acrylics include polymethyl methacrylate (PMMA). Exemplary natural fibers include elasin, keratin, silk, hydroxyl apatite (HA), collagen, and chitosan. Exemplary metals include stainless steel, titanium, titanium alloys, cobalt, nickel titanium alloy (nitinol), and tantalum. Exemplary ceramics include zirconia, alumina, and silica.

In one embodiment, three-dimensional woven material 200 is a gradient woven material. A gradient woven material is defined as a material which includes a first layer of a first stiffness, a second layer of a second stiffness, and one or more layers between the first layer and the second layer having a stiffness between the first stiffness and the second stiffness. In one embodiment, the first layer is a first end layer of the a woven material and the second layer is a second end layer of the woven material. In one embodiment, the gradient woven material includes at least one of the end layers of the overall woven material. In one embodiment, the gradient woven material is interposed between additional layers of a woven material.

The first layer, the second layer, and the interposed layers may include a single material or multiple materials. Further, the out of layer warp fiber 206 may have a stiffness generally the same as the layer it is woven in or a stiffness generally the same as the layer which it couples to the layer it is woven in.

An exemplary gradient material will be presented with reference to FIG. 11. In general layers made of metallic fibers are stiffer than layers made of ceramic fibers, layers made of ceramic fibers are stiffer than layers made of thermoplastic fibers, layers made of thermoplastic fibers are stiffer than layers made of hydrophilic hydrogels.

Layer 210 of three-dimensional woven material 200 includes a plurality of weft fibers 202A, a plurality of in layer warp fibers 204A, and a plurality of out of layer warp fibers 206A. The plurality of weft fibers 202A, and the plurality of in layer warp fibers 204A are metallic fibers and provide layer 210 with generally a first stiffness.

Layer 212 of three-dimensional woven material 200 includes a plurality of weft fibers 202B, a plurality of in layer warp fibers 204B, and a plurality of out of layer warp fibers 206B. The plurality of weft fibers 202B and the plurality of in layer warp fibers 204B are approximately fifty percent metallic fibers and approximately fifty percent thermoplastic fibers and provide layer 212 with generally a second stiffness, lower than the first stiffness of layer 210. In one embodiment, all of the weft fibers 202B are one of metallic fibers and thermoplastic fibers and all of the in layer warp fibers are the other of metallic fibers and thermoplastic fibers. In one embodiment, at least one of weft fibers 202B and in layer warp fibers 204B are a blend of metallic fibers and thermoplastic fibers. The plurality of out of layer warp fibers 206A of layer 210 may either be metallic fibers (similar to layer 210) or a blend of metallic and thermoplastic fibers (similar to layer 212).

Layer 214 of three-dimensional woven material 200 includes a plurality of weft fibers 202C, a plurality of in layer warp fibers 204C, and a plurality of out of layer warp fibers 206C. The plurality of weft fibers 202C and the plurality of in layer warp fibers 204C are generally thermoplastic fibers and provide layer 212 with generally a third stiffness, lower than the second stiffness of layer 212. The plurality of out of layer warp fibers 206B of layer 212 may either be thermoplastic fibers (similar to layer 214) or a blend of metallic and thermoplastic fibers (similar to layer 212).

Layer 216 of three-dimensional woven material 200 includes a plurality of weft fibers 202D, a plurality of in layer warp fibers 204D, and a plurality of out of layer warp fibers 206D. The plurality of weft fibers 202D and the plurality of in layer warp fibers 204D are approximately fifty percent hydrophilic hydrogel fibers and approximately fifty percent thermoplastic fibers and provide layer 216 with generally a fourth stiffness, lower than the third stiffness of layer 214. In one embodiment, all of the weft fibers 202D are one of hydrophilic hydrogel fibers and thermoplastic fibers and all of the in layer warp fibers are the other of hydrophilic hydrogel fibers and thermoplastic fibers. In one embodiment, at least one of weft fibers 202D and in layer warp fibers 204D are a blend of hydrophilic hydrogel fibers and thermoplastic fibers. The plurality of out of layer warp fibers 206C of layer 214 may either be thermoplastic fibers (similar to layer 214) or a blend of hydrophilic hydrogel fibers and thermoplastic fibers (similar to layer 216).

Layer 218 of three-dimensional woven material 200 includes a plurality of weft fibers 202E and a plurality of in layer warp fibers 204E. The plurality of weft fibers 202E and the plurality of in layer warp fibers 204E are generally hydrophilic hydrogel fibers and provide layer 218 with generally a fifth stiffness, lower than the fourth stiffness of layer 216. The plurality of out of layer warp fibers 206D of layer 216 may either be hydrophilic hydrogel fibers (similar to layer 218) or a blend of hydrophilic hydrogel fibers and thermoplastic fibers (similar to layer 216).

Straight warp fibers 208A are provided generally between layers 210 and 212. Straight warp fibers 208A may be made from fibers having the same materials as layer 210 or the same materials as layer 212. In a similar fashion straight warp fibers 208B are provided generally between layers 212 and 214;

straight warp fibers 208C are provided generally between layers 214 and 216; and straight warp fibers 208D are provided generally between layers 216 and 218.

Any given straight warp fiber 208, weft fiber 202, in layer warp fiber 204, and out layer warp fiber 206, may be replaced with one or more sensors, such as an optical fiber 166 including optical sensors. Further, any given straight warp fiber 208, weft fiber 202, in layer warp fiber 204, and out layer warp fiber 206, may support on or more sensors. Exemplary supported sensors include resonant circuits with digital identifiers (see FIG. 15) and resonant circuits 122.

In one embodiment, a three-dimensional woven material 246 forms a portion of an orthopedic implant 250. Implant 250 is coupled to a femur bone 249 of a knee joint 248. Woven material 246 includes a first layer 252 positioned adjacent bone 249, a second layer 254, and a third layer 256. Third layer 256 may act as a bearing surface 258. In one embodiment, third layer 256 is coated with a resin, epoxy, or a biological gel to form bearing surface 258. In one embodiment, the polymer fibers of the third layer 256 form the bearing surface 258. In one embodiment, first layer 252 includes metallic fibers, third layer 256 includes polymer fibers, and second layer 254 is a transitional layer, such as thermoplastic fibers and/or ceramic fibers. In one embodiment, at least one of first layer 252, second layer 254, and third layer 256 support one or more sensors. An exemplary sensor supported by first layer 252 would be a bone in-growth sensor.

Exemplary bone in-growth sensors include resonant circuits 122. Turning to FIG. 14, to measure bone-in growth, a region 125 between the capacitive plates of capacitor 126 is aligned with a region of expected bone in-growth. As bone grows into region 125, the dielectric constant of capacitor 125 changes which alters the frequency of the response signal 132 provided by resonant circuit 122. It should be noted that capacitor 126 does not need to be two plates separated by a dielectric. In one embodiment, a first portion of capacitor 126 may be positioned side-by-side to, but separated from, a second portion of capacitor 126. Changes in the dielectric material adjacent the first portion and the second portion would cause a change in the capacitance of capacitor 126.

Although capacitor 126 is described as the mechanism to measure bone in-growth, either resistor 128 or inductor 124 may be used instead. Changes to the inductor would result in a change in the inductance of the circuit which would have an effect on the response signal. Changes to the resistance would result to changes in the response signal, such as how long circuit 122 rings (dampen out quickly").

A resonant circuit with a digital identifier 260 (see FIG. 15) may also be used as a bone in-growth sensor. Resonant circuit 260 may also monitor the dielectric constant of capacitor 126. However, unlike resonant circuit 122, resonant circuit can send a signal with a unique identifier identifying itself and an indication of the dielectric constant of capacitor 126. The unique identifier and the message packet for signal 132 are controlled by a controller or processor 262 powered by the received signal 130. In one embodiment, controller 262 is a passive device like a surface acoustic wave (SAW) device which burst back a modulated signal, unique identifier. In this case all resonant circuits may be tuned to the same excitation frequency and the SAW device of each circuit would burst back a modulated signal at a particular frequency. The SAW device includes a converter to generate DC energy to power the logic of the controller and then provide response signal. The response can be sent out with the same antenna (between excitation signals) or a different antenna. In one embodiment, a resonant circuit includes a controller which includes an active device, like a mixed-signal application specific integrated circuits (ASIC). The inclusion of a mixed signal ASIC results in a semi-passive device.

Another resonant circuit is shown in FIG. 16 which includes a local power source 264 for controller 262 which either supplements the power from the received signal or provides power for intermittent readings of strain or bone in-growth. An exemplary power source is a battery. Another exemplary local power source includes a piezoelectric member. It is believed that another potential local power may be a plurality of zinc oxide nanowires discussed in more detail in "Piezoelectric Nanogenerators Based on Zinc oxide Nanowire Arrays," Science, Apr. 14, 2006. In one embodiment, the local power source may scavenge energy from the received excitation signal.

An exemplary sensor supported by one of first layer 252, second layer 254, and third layer 256 is a strain sensor. Exemplary strain sensors include resonant circuits 122. Referring to FIG. 17, a resonant circuit 122 is shown wherein the antenna 124 is wrapped around a weft fiber 202. As weft fiber 202 is compressed or stretched along its length, the frequency response of resonant circuit 122 is altered. In one embodiment, a resistive element of circuit 122 is wrapped around a weft fiber 202 and changes in the resistance of circuit 122 provides an indication of the strain on the fiber. In one embodiment, a capacitive element of circuit 122 is wrapped around a weft fiber 202 and changes in the capacitance of circuit 122 provides an indication of the strain on the fiber.

Referring to FIGS. 18-21, an end view of a portion of an orthopedic implant 300 is shown. Implant 300 may be a part of a knee joint 248, like implant 250. Over time it is possible for implant 300 to experience wear due to the forces exerted thereon. Orthopedic implant 300 may be made of a woven material and/or other materials.

Figure 19:
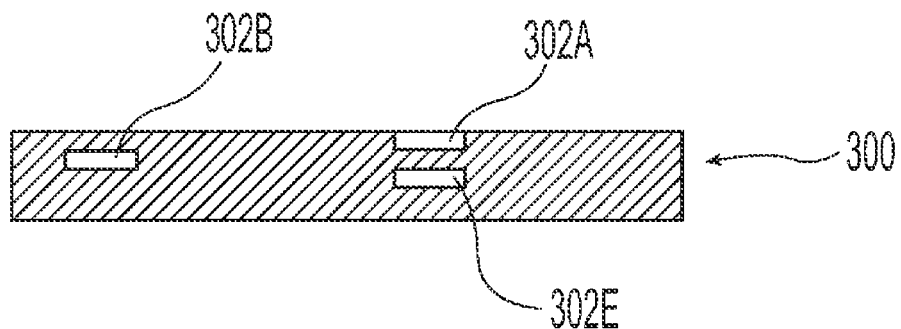
FIG. 19 is a sectional view of FIG. 18 illustrating sensors at various depths.

Implant 300 includes a plurality of sensors 302A-E (sensor 302E shown in FIG. 19) which provide an indication of wear of the orthopedic implant 300. In one embodiment sensors 302A-E are resonant circuits 122. In one embodiment, sensors 302A-E are RFID tags 260. The location of each sensor is mapped to a location on the implant. As such, once interrogated each sensor then provides an indication of wear at that location. As shown in FIG. 19, sensor 302E is at a deeper depth than sensors 302A and 302B.

Figure 20:
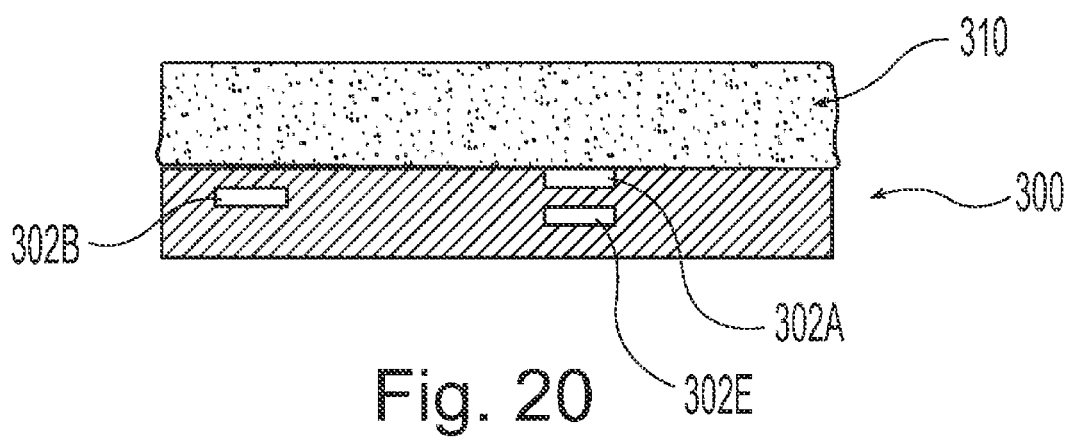
FIG. 20 is the sectional view of FIG. 19 illustrating sensors at various depths and a bone positioned proximate an upper surface of the orthopedic implant.

In one embodiment, sensors 302A-E are resonant circuits 122 and are interrogated by interrogation system 150. Each resonant circuit 122 provides a response signal 132 in response to its respective interrogation signal 130. If all sensors provide a response signal 132 than implant 300 has not experienced any appreciable wear. This is shown in FIG. 20 wherein a bone 310 is resting upon implant 300.

Figure 21:
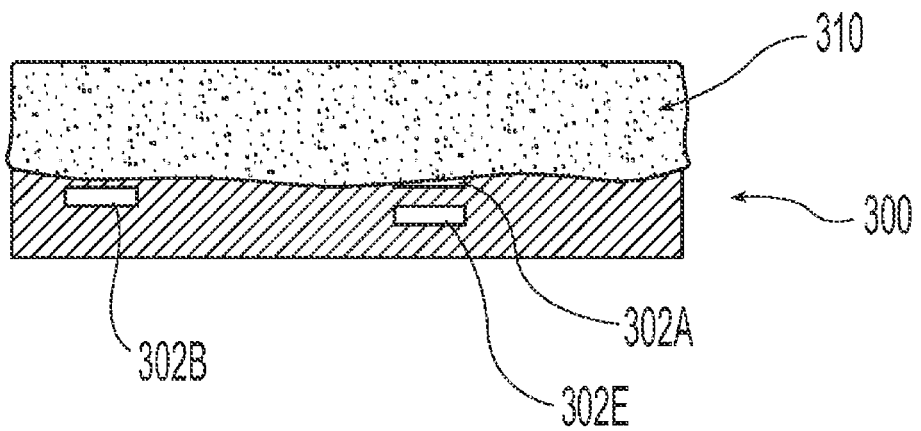
FIG. 21 is a representation of the sectional view of FIG. 20 showing the wear of the orthopedic implant.

Referring to FIG. 21 bone 310 (or other items) has over time worn portions of implant 300. As illustrated in FIG. 21, bone 310 has destroyed sensor 302A. Upon the next interrogation sensor 302A will not respond. An operator or software application based on a knowledge of the location of sensors 302A is able to determine that implant 300 is worn in the area of sensor 302A. However, since sensor 302E still provides a signal in response to the interrogation, it is known that the wear of implant 300 has not reached the depth of sensor 302E.

Although the invention has been described in detail with reference to certain preferred embodiments, variations and modifications exist within the spirit and scope of the invention as described and defined in the following claims.

The invention claimed is:

1. An orthopedic implant for placement in a cavity formed in a bone, said cavity having a predetermined shape, said orthopedic implant comprising:

a flexible body having an opening, said flexible body having an inflated state wherein said body has an outer shape generally corresponding to said predetermined shape formed in said bone and a non-inflated shape wherein said outer shape has a smaller envelope than said inflated state;

a plurality of sensors supported by said flexible body, said plurality of sensors providing an indication of whether said flexible body is in said inflated state or said non-inflated state, wherein said plurality of sensors are configured to detect a presence of a fold in said flexible body, wherein said fold is detected based on said relative position of a first sensor to a second sensor, wherein said first sensor and said second sensor are passive sensors interrogated by an external device, wherein said first sensor and said second sensor are each resonant circuits which provide said indication based on a separation between said first sensor and said second sensor, and wherein when said first sensor and said second sensor are spaced a first distance apart said first sensor resonates in response to a first frequency from said external device and said second sensor resonates in response to a second frequency from said external device and when said first sensor and said second sensor are spaced less than said first distance apart said first sensor and said second sensor resonate together in response to a third frequency from said external device; and a filler, said filler being positioned in said flexible body and causing said flexible body to transition from said non-inflated state to said inflated state.

2. The orthopedic implant of claim 1, wherein said filler is a polymer based material.

3. The orthopedic implant of claim 1, wherein said external device interrogates said plurality of sensors through a frequency range including said first frequency, said second frequency, and said third frequency.

4. A method of implanting an orthopedic implant in a cavity having a predetermined shape formed in a bone, said method comprising the steps of:
providing a flexible body which is inflatable to a first state having an outer shape generally corresponding to said predetermined shape formed in said bone;
positioning said flexible body in said cavity having said predetermined shape formed in said bone;
inflating said flexible body; and
sensing whether said flexible body is inflated to said first state, including the steps of:
providing a plurality of passive sensors supported by said flexible body;
interrogating said plurality of passive sensors to determine whether said flexible body is inflated to said first state, including the steps of:
passing a first plurality of radio frequency frequencies through said bone;
receiving a second plurality of radio frequencies from said plurality of sensors; and
determining whether said flexible body is inflated to said first state based on said received second plurality of radio frequencies.

5. The method of claim 4, wherein said step of inflating said flexible body includes filling an interior of said flexible body with a filler which hardens over time.

6. A woven material for use within the body, the woven material comprising:
a first woven layer having a first plurality of weft fibers and a first plurality of in layer warp fibers, said first layer having a first stiffness;
a second woven layer having a second plurality of weft fibers and a second plurality of in layer warp fibers, said second layer having a second stiffness generally less than said first stiffness;
a third woven layer having a third plurality of weft fibers and a third plurality of in layer warp fibers, said third layer having a third stiffness generally less than said second stiffness;
a first plurality of out of layer warp fibers which couple together said first layer and said second layer;
a second plurality of out of layer warp fibers which couple together said second layer and said third layer
a fourth layer having a fourth stiffness and coupled to said third layer opposite said second layer;
a fifth layer having a fifth stiffness and coupled to said fourth layer opposite said third layer;
a third plurality of out of layer warp fibers which couple together said third layer and said fourth layer; and
a fourth plurality of out of layer warp fibers which couple together said fourth layer and said fifth layer,
wherein said first plurality of weft fibers and said first plurality of in layer warp fibers are metallic fibers and wherein said second plurality of weft fibers and said second plurality of in layer warp fibers are a blend of metallic fibers and non-metallic fibers.

7. The woven material of claim 6, further comprising a fourth layer having said first stiffness and coupled to said first layer opposite said second layer.

8. The woven material of claim 6, wherein said third plurality of weft fibers and said third plurality of in layer warp fibers are polymeric fibers and wherein said blend includes and polymeric fibers.

9. The woven material of claim 6, wherein at least one of said first layer, said second layer, and said third layer support a plurality of sensors.

10. The woven material of claim 9, wherein said plurality of sensors provide an indication of a shape of the woven material.

11. The woven material of claim 6, wherein said plurality of sensors are passive radio frequency sensors.

* * * * *